United States Patent [19]
Hall et al.

[11] Patent Number: 5,361,758
[45] Date of Patent: Nov. 8, 1994

[54] METHOD AND DEVICE FOR MEASURING CONCENTRATION LEVELS OF BLOOD CONSTITUENTS NON-INVASIVELY

[75] Inventors: Jeffrey W. Hall, Lindsay; T. E. Cadell, Waterloo, both of Canada

[73] Assignee: CME Telemetrix Inc., Waterloo, Canada

[21] Appl. No.: 785,430

[22] Filed: Oct. 9, 1991

Related U.S. Application Data

[63] Continuation-in-part of Ser. No. 362,342, Jun. 7, 1989, abandoned, which is a continuation-in-part of Ser. No. 345,304, May 1, 1989, abandoned.

[30] Foreign Application Priority Data

Jun. 9, 1988 [GB] United Kingdom ............ 8813658.5

[51] Int. Cl.$^5$ ................................................ A61B 5/00
[52] U.S. Cl. .................................. 128/633; 128/632; 128/664; 128/665
[58] Field of Search ........................... 129/632–634, 129/664, 665, 395, 397, 398

[56] References Cited

U.S. PATENT DOCUMENTS

| | | | |
|---|---|---|---|
| 4,267,844 | 5/1981 | Yamanishi | 128/633 |
| 4,407,290 | 10/1983 | Willer | 128/665 |
| 4,427,889 | 1/1984 | Müller | 128/633 |
| 4,655,225 | 4/1987 | Dähne et al. | 128/633 |
| 4,700,708 | 10/1987 | New, Jr. et al. | 128/633 |
| 4,723,554 | 2/1988 | Oman et al. | 128/633 |
| 4,737,628 | 4/1988 | Lovou | 128/395 |
| 4,805,623 | 2/1989 | Jölsis | 128/633 |
| 4,938,218 | 7/1990 | Goodman et al. | 128/633 |

FOREIGN PATENT DOCUMENTS 316812 5/1989 European Pat. Off. ............ 128/633

Primary Examiner—David M. Shay
Attorney, Agent, or Firm—Daryl W. Schnurr

[57] ABSTRACT

A non-invasive device and method for monitoring concentration levels of blood and tissue constituents within a living subject such as a human or animal utilizes a polychromatic light source that emits light over a broad spectrum of wavelengths in the near infrared range. The light is passed through, or reflected from, a part of the subject such as a finger, ear lobe or other part of the body. That light is then separated into its various components by means of a grating or prism, and the near infrared band is focussed onto a linear array detector. A microprocessor uses the output of the array detector to measure the light transmitted (T), calculate the absorbance (log 1/T) and calculate the second derivative of the absorbance. A calibration equation is used for each constituent to be monitored to convert the second derivative measurements to a concentration level for that constituent. The device is programmed to take measurements between heart beats and to adjust for the temperature of the sample being taken. The device can be used to determine levels of various blood and tissue constituents, including glucose, cholesterol, alcohol, blood gases and various ions. The device is simple to use, painless and does not cause any physical discomfort, skin irritation or present any risk of infection to the user. The device can be used for clinical use or for home use and the memory of the microprocessor can be used to assist with record keeping and with dosage calculations. Previous non-invasive devices are not sufficiently accurate or convenient to use to replace the invasive testing systems presently used.

33 Claims, 4 Drawing Sheets

METHOD AND DEVICE FOR MEASURING CONCENTRATION LEVELS OF BLOOD CONSTITUENTS NON-INVASIVELY

This is a continuation-in-part application of application Ser. No. 07/362,342 filed Jun. 7, 1989, now abandoned, which is a continuation-in-part application of application Ser. No. 07/345,304 filed May 1, 1989, now abandoned.

BACKGROUND OF THE INVENTION

1. Field of the Invention

This invention relates to a non-invasive device and method for monitoring concentration levels of blood constituents in living subjects such as humans or animals, using the near infrared portion of the light spectrum and, in particular, relates to a device and method suitable for continuously, or on demand, monitoring concentration levels of blood constituents within the human body.

2. Description of the Prior Art

Previous devices for non-invasively monitoring concentrations of blood constituents of a patient are known. Usually, a sensor is used to externally measure either the concentration of the constituent in gases emitted by the body; the concentration contained in perspiration; or the concentration contained in body fluids such as tears, saliva, or urine samples; or, alternatively, the blood constituent is measured using radiation passed through a part of the patient's body such as the earlobe. However, of the previous radiation devices, some have a radiation source which emits light in one wavelength only and are therefore not accurate or broadly applicable enough for practical use. Other previous devices have more than one light source but have only a limited number (three) of measuring wavelengths. Some of these previous devices have had a number of discrete wavelength sources obtained through use of a broad-band lamp whose light is optically coupled through a number of light filters, each with its own designated transmission wavelength, to the test sample. Some of these previous devices must measure both the intensity changes in the range of transmission wavelength and the changes in intensity distribution. Further, some previous devices are controlled to take a series of measurements at successively higher or lower wavelengths. This can be extremely time consuming. Further, some previous devices do not take into account changes in the thickness of one patient's earlobes compared to that of other patients or the change in size of a patient's earlobes or the change in the transmission path length due to the pulsing of blood through the patient; or, they do not take into account temperature variations in the earlobes from patient to patient; or, the results fluctuate with prolonged operation. Previous non-invasive devices are not sufficiently accurate to be used in place of invasive techniques in the measurement of blood constituent concentration levels by patients; or, they are designed to measure for one component only and must be physically changed to measure for a different component; or, the device takes an unreasonably long time to produce a result; or, they cannot produce results in an easy-to-use form; or, they cannot measure the results of two or more constituents simultaneously. Obviously, if the device gives an inaccurate reading, disastrous results could occur for the patient using the device to calculate, for example, dosages for insulin administration.

Invasive techniques of measuring blood constituents are, of course, in common usage. These techniques are painful, potentially dangerous and expensive to operate. The normal procedure is to obtain a blood sample from a vein and this sample is then tested in a medical laboratory, using a number of chemical procedures to measure each constituent separately. Alternatively, home glucose testing uses a finger puncture that is spotted onto an enzyme-based semi-permeable membrane test strip and is allowed to react for a certain length of time, with insulin administration then based upon either a visual colour comparison with a standard colour chart or by means of a more accurate and unambiguous spectroscopic technique (for example reflectance). There is a risk of infection and sometimes a patient can develop a rash when these invasive techniques are used.

Summary of the Invention

It is an object of the present invention to provide a device for monitoring the concentration levels of one particular constituent or, alternatively, of measuring the concentration level of several different constituents simultaneously, said device producing results in a short time period that are highly accurate and compare favourably to invasive techniques.

A non-invasive device measuring concentration levels of blood and tissue constituents in a living subject such as a human or animal uses a polychromatic light source that emits a broad spectrum of light in the near infrared range. The light source is coupled to and powered by a stabilized power source and said device has a receptor shaped so that part of the subject can be placed in contact with said receptor. The receptor has means for eliminating extraneous light and is located relative to said light source so that when part of said subject is placed in contact with said receptor, said light source can be activated and light from said light source, at a continuum of wavelengths, is directed onto said part. There are means coupled to the device for collecting a continuum wavelengths of said light after said light has been directed onto said part and means coupled to the device for dispersing said collected light over said broad spectrum into a dispersed spectrum of component wavelengths of said collected light and means coupled to the device for taking absorbance measurements from at least one of transmitted and reflected light from said collected light at several different wavelengths simultaneously. There are means for transforming said measurements over said to enhance dispersed spectrum. There are means for transforming said measurements over said dispersed spectrum; measurement of concentration of at least one constituent from other constituents by using a calibration equation for said at least one constituent and means coupled to the device for determining the concentration level of said at least one constituent of said blood and then producing a result for each concentration level determined.

In a method for measuring concentration levels of blood constituents within a living subject such as humans or animals, there is used a polychromatic light source that emits a broad spectrum of light in the near infrared range from 650 nm to 2700 nm. The method comprises the steps of directing light at a continuum wavelengths simultaneously onto a part of said subject, collecting the continuum of light after said light has been directed onto said part, focusing the collected light onto a grating, dispersing said continuum of light into a dispersed spectrum a dispersed spectrum of component wavelengths of said collected light onto a linear array detector, said linear array detector taking measurements of at least one of transmitted and reflected light from said collected light in said near infrared range simultaneously said continuum of wavelengths over said dispersed spectrum, scanning said linear array detector and passing said measurements to a microprocessor, taking a reference set of measurements transforming said measurements over said dispersed spectrum, to enhance the measurement of connectration of at least one constituent from other constituents using a calibration equation, determining the concentration level of said at least one constituent of said blood and tissue and producing a result for each concentration level determined.

DESCRIPTION OF A PREFERRED EMBODIMENT

The near infrared region of the electromagnetic spectrum is generally considered to be the spectral interval extending from 650 nm through to 2700 nm and measurements are preferably taken in the 700 nm to 1100 nm range. Absorbtion bands observed in this interval are primarily the combination and overtone bands of the fundamental infrared bands. Although very weak in intensity, being typically less than one-tenth in intensity of the fundamental infrared bands, these bands are considered to be quite analytically useful because nearly all chemical species exhibit characteristic absorption bands in this spectral interval. The near infrared region is particularly well-suited to in vivo diagnostic applications because human tissue is essentially transparent to the incident radiation and therefore sufficient penetration of the radiation is possible to allow accurate quantitative analysis.

Figure 1:
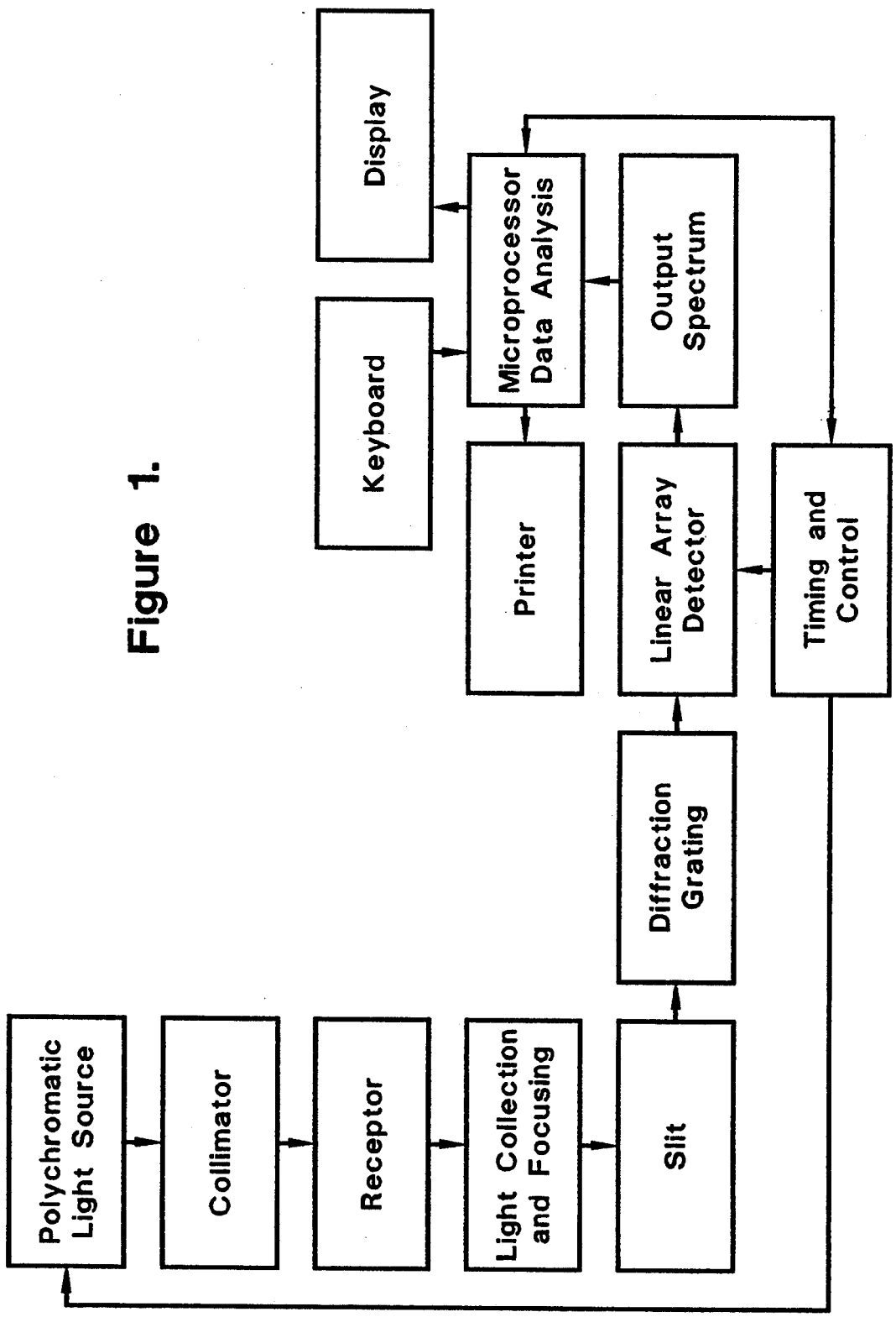
FIG. 1 is a block diagram showing the relationships for various components of a device for non-invasively monitoring the concentration levels of blood constituents.

As shown in FIG. 1, a non-invasive device for continuously monitoring concentration levels of blood and tissue constituents has a polychromatic light source. The light source can emit light over a very wide bandwidth including light in the near infrared spectrum. The light from the light source passes first through a collimator, which is a collection of lenses that concentrate the light into a narrow parallel beam directed at the receptor. The receptor is shaped to receive within it that part of the subject, for example, a finger or ear of a human. Alternatively, the receptor could be shaped so that the part of the human or animal, onto which the light is to be directed, is placed near the receptor rather than within the receptor. In any event, the part is in contact with the receptor. The light is directed onto the finger or ear and is dispersed by said finger or ear. The dispersed light is collected by lenses and directed through a slit to diffraction means. Preferably, the diffraction means is a diffraction grating or a holographic grating. Alternatively, the means for collecting said light after said light is directed onto said receptor are fibre optics that transmit said light to diffraction means. The collected light can be light that has passed through the finger or ear or has reflected off the finger or ear or a combination thereof. Preferably, the collected light is light that has passed through said parts of the subject. The light from the grating disperses the light into its component wavelengths so that the light in the infrared region falls along the length of a linear array detector. The array detector has a series of diodes and is electronically scanned by a microprocessor to measure the charge accumulated on each diode, the charge being proportional to the intensity of light for each wavelength transmitted through or reflected from the tissue in the receptor. The detector is connected to the microprocessor, producing an output spectrum, with the microprocessor analyzing the measurements and ultimately producing a result for each concentration level determined. The result can be shown on a display and/or printed on a printer. The keyboard allows a user to control the device, for example, to specify a particular constituent to be measured. The timing and control is activated by the microprocessor to control the device, for example, to determine number and timing of measurements.

The polychromatic light source can be a quartz-halogen or a tungsten-halogen bulb and is powered by a stabilized power source, for example, a DC power supply, or by a battery. Preferably, the linear array detector has at least ten elements. This polychromatic light source may be a tungsten-halogen lamp or it may be a collection of LEDs or other light sources selected to emit radiation in the range of 650 to 1100 nm. It should be noted that after activation of the light source, the scanning detector is read so that light is passed through the receptor and measured by the detector through the taking of a series of measurements at a selected wavelength. Measurements on this wavelength are sensitive to increased plethysmographic volume (i.e. path length) and so measure the heart pressure pulse. The microprocessor control activates and scans the linear array detector only after a detected pulse has occurred and the full spectrum measurements are then taken for the light after it passes through the receptor. Scanning is stopped when another pulse is detected on the selected wavelength. In other words, measurements are taken only when the blood pressure in the finger or ear or other part of the person is at a constant level. This ensures that the path length of the tissue through which the light passes will be uniform. Pulse detection can be accomplished by conventional means including monitoring plethysmographic volume (i.e. use of light or pressure detection means to monitor changes in volume of the body part) or by sonograms of heart activity or electrocardiograms.

In a further variation, the device can take all measurements regardless of the pulse of the subject. The microprocessor can then be controlled by computer software to select those measurements that are taken between pulses and to base the calculation of the concentration levels on the selected measurements. In a further variation, the measurements upon which the results are based, could be taken during pulses.

The receptor has means for eliminating extraneous light. For example, where a finger is the part of a human through which the light passes, the receptor has an oblong shape similar to but larger than the shape of the finger. The means for eliminating extraneous light from the receptor is a flexible ring that surrounds an entrance to the receptor. When the finger is inserted, the flexible ring forms a seal around the finger when the finger has been inserted into the receptor. All surfaces within the device, including surfaces within the receptor are made non-reflective to minimize stray light.

The lenses to collect the light after it is transmitted through (or is reflected from) the finger or other body part as well as the slit can be omitted and replaced by fibre optics to direct the light onto the diffraction grating. After the measurements are taken for the transmittance and/or reflectance, the log of the inverse of these measurements is taken, that is, log 1/T and log 1/R, where T and R represent the transmittance and reflectance respectively. A reference set of measurements is taken of the incident light, being the light generated in the device when no part of the subject is in contact with the receptor. The absorbance is then calculated when a part of the subject, such as the finger, is in contact with the receptor as a ratio of measurements compared to the reference set of measurements.

The second derivative of the said measurements is taken in order to reduce any variation in the result that will be caused by a change in path length for the light. When the device is in use, various users will have fingers of different size and thickness depending on the person being tested. The effect of the different path length can be reduced by taking the second derivative of the measurement. Also, the calculation of the second derivative of the measurements sharpens the peaks of the blood and tissue constituents for the graph of the second derivative versus wavelength. The calculation of the second derivative does not eliminate the effect of changes in path length caused by the pulse of the subject. While there are other means of manipulating the data obtained from the measurements of reflectance and transmittance, which will produce the same results as that obtained by taking the second derivative, the taking of the second derivative is the preferred means.

The diffraction grating (which may be a holographic diffraction grating) is used to spatially spread the spectrum of the collected light onto the scanning detector. The linear array detector is typically a 256 element photo diode array.

The noise levels within the device are reduced by the multiple scanning technique whereby the linear array detector takes a number of measurements and then averages the results. For example, the detector can scan the entire spectrum of interest between heart beats and then average the results. Preferably, the linear array detector scans the entire spectrum of interest many times per second for several repetitions of said entire spectrum ranging from approximately 8 to approximately 64 repetitions and the microprocessor then averages the results. The device can be used to determine the concentration of only one component of the sample in the receptor or several components derived from the same averaged spectra. Of course, as the number of components that are being measured increases, the time taken to display the results increases, due to computer processing time and the time to print the results. However, the increase in time due to additional analytes is still much less than two minutes. The time for taking measurements (at several different wavelengths simultaneously through many repetitions and then averaging the results) is usually approximately 3 minutes and is always less than 5 minutes. The time depends on the number of repetitions and the number of constituents being analyzed. Taking measurements quickly is particularly important when children are the subjects as they find it very difficult to keep their finger stationary, even for a brief period of time.

The calibration equation by which the blood glucose was computed was derived from a least squares best fit of the calibration spectral data to the actual measured levels of blood glucose obtained coincident with the recording of the spectra. The validation of the calibration equation is its ability to predict results for additional subjects in a manner similar to that shown in FIG. 4. The particular wavelengths for absorbance were chosen to minimize the standard error of measurement. The equation so generated had the form of:

$$Y = k_0 + k_1(A_{2d(1002)}) + k_2(A_{2d(890)})$$

Where
   Y was the concentration of glucose, and
   $k_0$, $k_1$, and $k_2$ were constants, and
   $A_{2d(1002)}$ and $A_{2d(890)}$ were measured second derivative values at wavelengths of 1002 and 890 nm respectively.

The constants $k_0$, $k_1$, and $k_2$ are dependent upon the instrumentation, including the optics and detectors and so must be determined independently for each instrument design. For the instrument of this embodiment the values were 26.12, 1595.142, and 1877.461 respectively. In the case of the absorbance at particular wavelengths, one of the factors governing selection of wavelengths was exclusion of wavelengths associated with hemoglobin and cytochrome in the range of approximately 700 nm to 800 nm since these were found to vary among individuals in such a way as to make a universal equation unrealizable. While measurements were taken at only two wavelengths, the concentration level of glucose could be determined by taking measurements at other wavelengths within the desired range or at more than two wavelengths.

The results obtained can vary with the temperature of the sample or finger of the user. Therefore, the device contains a temperature sensor so that the temperature of the sample can be measured rapidly at the time of the spectral sampling. This temperature sensor is typically a small-mass thermocouple. Computer software can then be used to allow the microprocessor to compensate for spectrum deviations due to the temperature. So as not to delay the production of results, the temperature sensor has a 150 to 200 millisecond response time.

The linear array detector is preferably a photo diode array that is positioned to intercept, across its length, the dispersed spectrum from the diffraction grating. The microprocessor is directed by software to scan the linear array detector and calculate the second derivative of the spectrum computed. The microprocessor can then calculate the concentration of the particular constituents being measured using the absorbance and second derivative values for a number of selected wavelengths. The calibration equation used for each constituent is determined by the analyte being measured.

The use of the second derivative calculation also eliminates base line shifts due to different path lengths or absorbing water bands, and in addition, enhances the separation of overlapping absorbtion peaks of different constituents of the mixture being analyzed.

Figure 2:
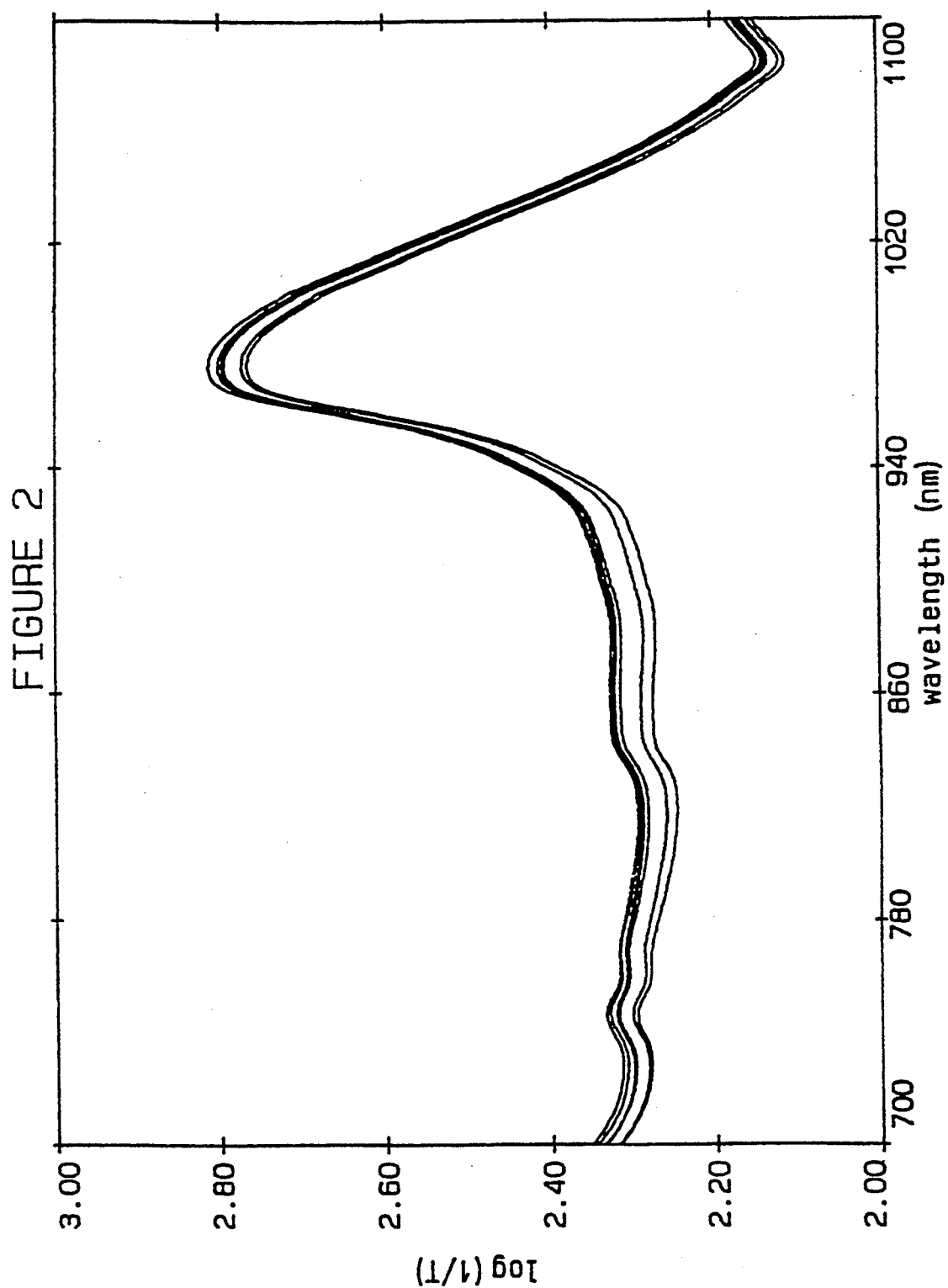
FIG. 2 is a graph of typical absorption spectrum (log 1/T) of glucose concentrations for various wavelengths obtained from fingertip measurements.

In FIG. 2, the typical absorbtion spectra (log 1/T), where T is the light transmitted, is shown for fingertip measurements of the variance of glucose concentrations with wavelength over the 700 nm to 1100 nm range. Seven measurements of absorbance through the finger over the wavelength range were taken over a three hour period. The measurements vary in degree of absorbance representing variations in the path length through the finger. The absorbance peak due to water occurs at approximately 970 nm to 980 nm.

Figure 3:
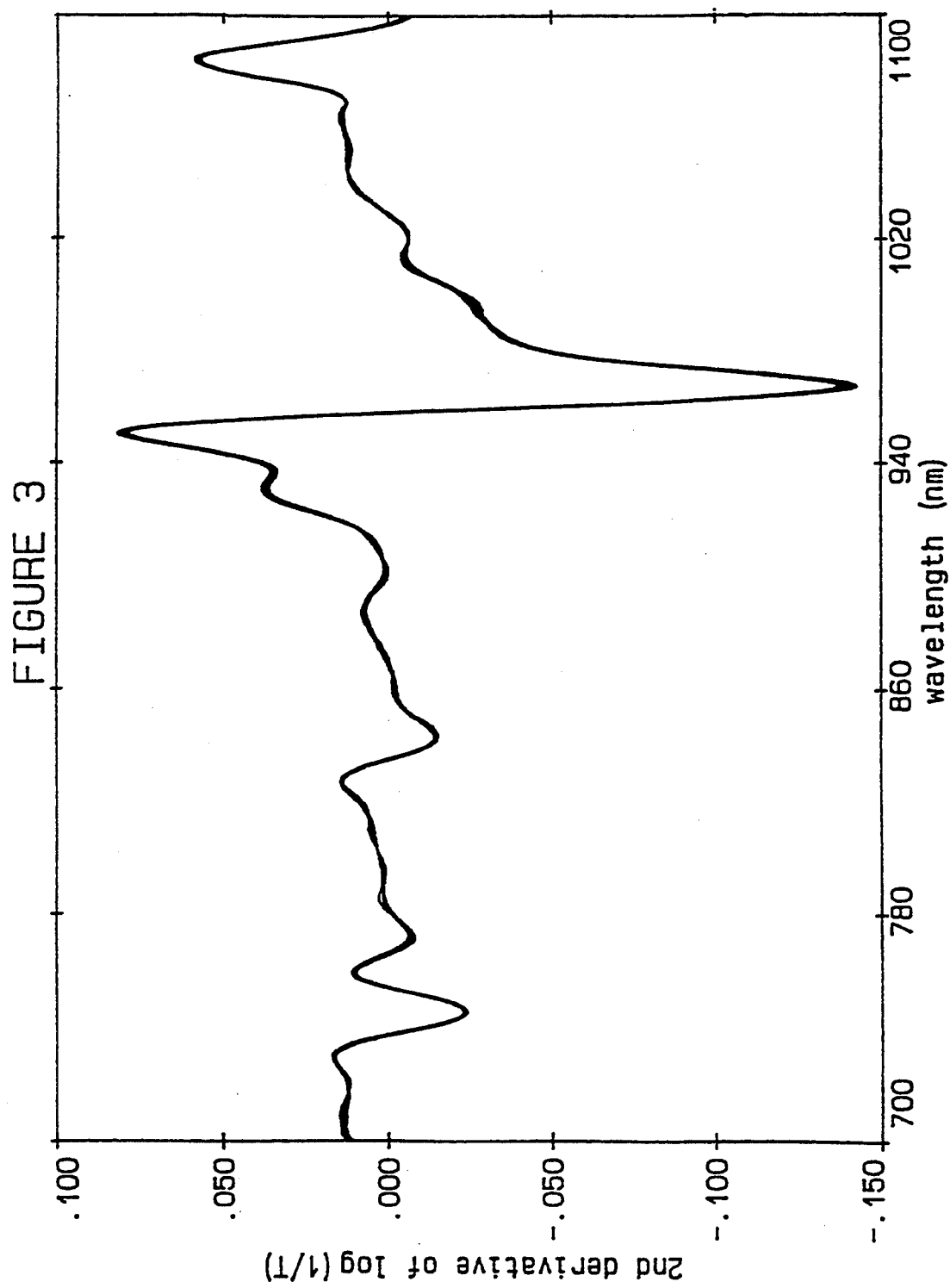
FIG. 3 is a graph showing the variance of the second derivative of the absorbance spectrum of FIG. 2 with wavelength.

In FIG. 3, there is shown the second derivative of the absorbance spectra shown in FIG. 2 over the same wavelength range. The second derivative calculation normalizes the absorbance data for differences in path length. Whereas there was a relatively wide variance of the curves shown in FIG. 2, the curves shown in FIG. 3 almost completely overlap with one another. In the water band data, being the 970 to 980 wavelength range, the curves completely overlap. The slight variation in the curves at various wavelengths as shown in FIG. 3 by the increasing thickness of the curve represents variations in the blood constituents themselves, for example, glucose, over the three hours of the glucose tolerance test. The data in FIG. 3 were analyzed to generate a calibration equation to compare the amount of glucose present using the non-invasive testing of the present invention with results obtained for the same subjects at the same time using invasive techniques. For each instrument design in accordance with the present invention, it will be necessary to establish a calibration equation for each constituent to be measured. A calibration equation for each constituent can be used for all instruments of the same design.

Figure 4:
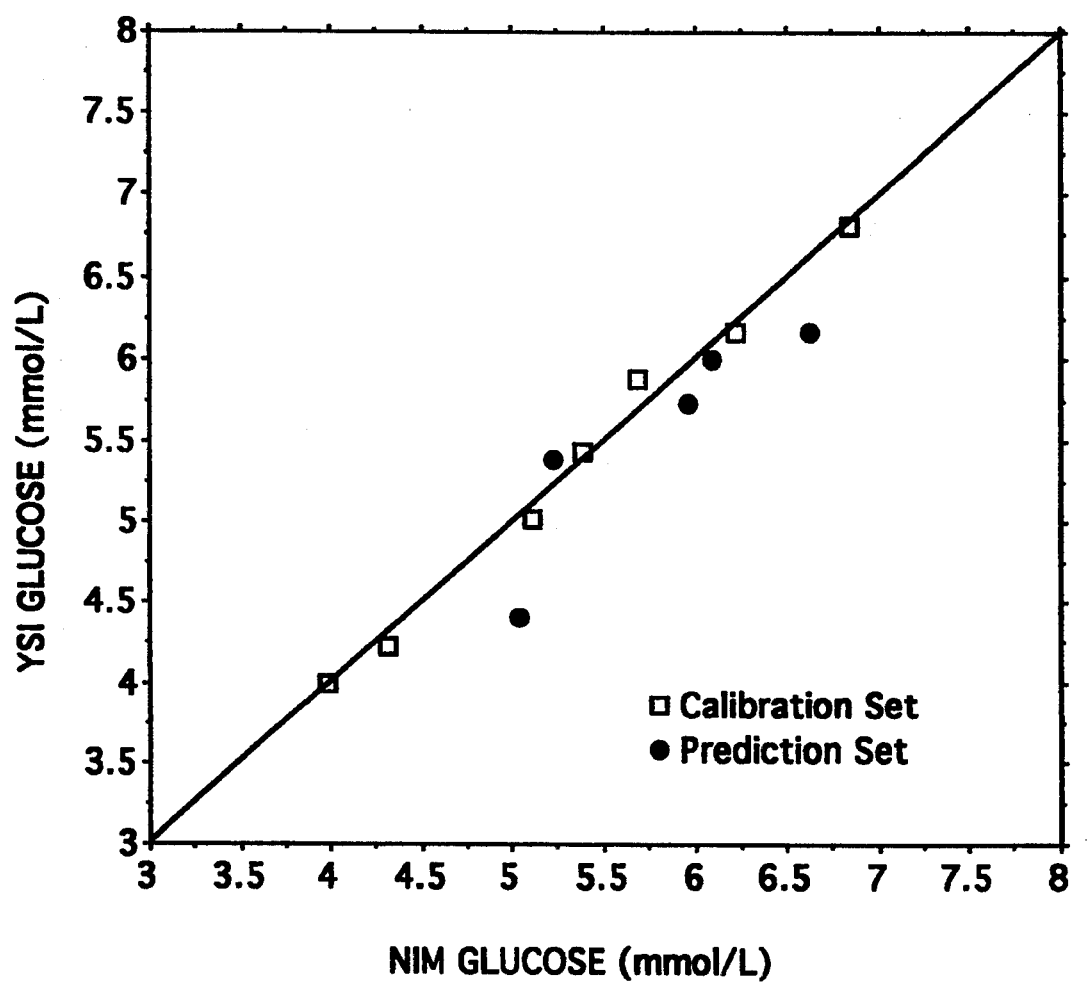
FIG. 4 is a graph showing the concentration level of glucose in blood obtained through invasive testing compared to results obtained through the use of the present invention.

In FIG. 4, there is shown the relationship between invasive glucose measurements (YSI) and non-invasive measurements (NIM) obtained using the method and device of the present invention. The calibration set of data are derived from the data shown in FIGS. 2 and 3 of the present application. The solid black line represents the least squares best fit line derived by computer for the calibration between the invasive and non-invasive results. The calibration set of results was obtained from actual measurements conducted on a human subject using the non-invasive technique of the present invention. The standard error of measurement for the calibration set of measurements over invasive techniques is 0.113 millimoles per liter. The prediction set of measurements is based on measurements taken from further subjects non-invasively, predicting the actual level of glucose concentration based on the calibration set and comparing the predicted value to the actual value by taking invasive measurements. The standard error prediction for these data is 0.291 millimoles per liter.

The microprocessor can collect up to one hundred spectra and can then immediately calculate the second derivative of the averaged results. Preferably, the results will be digitally displayed for the user. Also, by using the memory capacity of the microprocessor, a user can monitor trends by comparing the most recent result with previous results. For glucose measurements, this will be of great assistance to a diabetic in order to enable the diabetic to determine future insulin dosage requirements.

While examples, the graphs of FIGS. 2, 3 and 4, have been primarily related to measuring glucose concentrations, the device can be used to measure concentration levels of various other constituents found within the blood of humans or animals, for example, amino acid, nitrogen, blood oxygenation, carbon dioxide, cortisol, creatine, creatinine, glucose, ketones, lipids, fat, urea, amino acids, fatty acids, glycosolated hemoglobin, cholesterol, alcohol, lactate, $Ca^{++}$, $K^+$, $Cl^-$, $HCO_{3-}$ and $HPO_{4-}$, to name a few. Devices for determining glucose levels can be pocket-sized and will be safer, more accurate when used by unskilled persons, painless and much more convenient than invasive techniques presently being used. The same can be said for devices that measure cholesterol levels. As is well known, alcohol levels are presently measured by either taking a blood sample or a breath sample. Approved breathalyzers are extremely expensive and certain disposable parts must be used for sanitation purposes or are chemically "consumed" as part of the measurement. Also, presently, it is generally not possible for a potential driver to measure his or her blood alcohol level before driving. If measurement devices were available in a compact inexpensive form, potential drivers would be able to take a measurement before driving. With the device of the present invention, alcohol levels could be measured quickly and easily without any active participation by the person whose alcohol level is being measured. The device can even be used when the person being measured was unconscious. Presently, in the field of sports medicine, the level of lactate present in muscles requires a biopsy and blood test. When athletes are in training for an upcoming event, biopsies are impossible because of the damage that they cause to the muscle. With the device of the present invention, lactate levels can be determined non-invasively.

While the device of the present invention can be designed to measure one constituent, the device can also be designed to measure several constituents simultaneously. In fact, a primary application of the device will be for measuring ten to forty or more constituents that are now typically measured in a medical or hospital lab after a vial of blood is extracted from the human or animal. Further, this multi-constituent measurement can be completed and results displayed in seconds right in the doctor's office rather than received in days or weeks as is the practice today.

What we claim as our invention is:

1. A non-invasive device for measuring concentration levels of constituents of blood and tissue in a living subject such as a human or animal, said device comprising a polychromatic light source that emits a broad spectrum of light in the near infrared range, said light source being coupled to and powered by a stabilized power source, said device having a receptor shaped so that part of said subject can be placed in contact with said receptor, said receptor having means for eliminating extraneous light, said receptor being located relative to said light source so that when part of said subject is placed in contact with said receptor, said light source can be activated and light from said light source at a continuum of wavelengths is directed onto said part, means coupled to the device for collecting simultaneously a continuum of wavelengths over said broad spectrum after said light has been directed onto said part, means coupled to the device for dispersing said collected light over said broad spectrum into a dispersed spectrum of component wavelengths of said collected light, means coupled to the device for taking absorbance measurements from at least one of transmitted and reflected light from said collected light at several different wavelengths simultaneously over said dispersed spectrum, means coupled to the device for transforming said measurements over said dispersed spectrum to enhance measurement of concentration of at least one constituent from other constituents by using a calibration equation for said at least one constituent, means coupled to the device for determining the concentration level of said at least one constituent of said blood and then producing a result for each concentration level determined.

2. A device as claimed in claim 1 wherein the calibration equation is derived from a least square's best fit of spectral data obtained by said device to actual measured levels obtained coincidentally.

3. A device as claimed in claim 2 wherein the means for transforming said measurements to enhance measurement of concentration of at least one constituent from other constituents comprises mean for taking a log of an inverse of at least one of the transmitted and reflected light from said collected light and further taking a second derivative of said log of the inverse.

4. A device as claimed in any one of claims 1, 2 or 3 wherein the means for measuring at least one of the transmitted and reflected light from said collected light at several different wavelengths simultaneously is a linear array detector and a microprocessor, said linear array detector receiving said collected light after the collected light has been directed onto said part and collected, said microprocessor comprising means for scanning said linear array detector, said detector being connected to said microprocessor for taking said measurements.

5. A device as claimed in any one of claims 1, 2 or 3 wherein the means for dispersing said collected light into component wavelengths of said collected light is a grating.

6. A device as claimed in any one of claims 1, 2 or 3 wherein there are means for detecting a pulse within that part of the subject placed in contact with said receptor, there being means to control said device to use measurements taken immediately subsequent to the detection of a pulse and prior to a next pulse so that all measurements upon which a result is based are taken between pulses.

7. A device as claimed in claim 2 wherein the device has a temperature sensor for measuring the temperature at that part of the subject located in contest with the receptor with means for adjusting the measurements taken based on variations in said temperature.

8. A device as claimed in claim 7 wherein the temperature sensor is a thermo-couple designed with a fast response time, of less than 200 milliseconds, and there is a microprocessor to compensate for spectrum deviations due to temperature.

9. A device as claimed in any one of claims 1, 2 or 3 wherein said receptor is shaped to receive said part of the subject within said receptor and the means for collecting is a means for collecting transmitted light.

10. A device as claimed in any one of claims 1, 2 or 3 wherein the means for eliminating extraneous light from the receptor is a flexible seal surrounding an entrance to said receptor, said seal being small enough to form a light barrier around that part of the subject onto which light is directed.

11. A device as claimed in any one of claims 1, 2 or 3 wherein the means for collecting said light at several different wavelengths simultaneously after said light has been directed onto said part are lenses.

12. A device as claimed in any one of claims 1, 2 or 3 wherein the means for detecting a pulse is a means for monitoring plethysmographic blood pressure.

13. A device as claimed in any one of claims 1, 2 or 3 wherein the means for detecting a pulse is a means for detecting the pulse from a sonogram.

14. A device as claimed in any one of claims 1, 2 or 3 wherein the means for detecting a pulse is a means for detecting the pulse from a an electrocardiogram.

15. A device as claimed in any one of claims 1, 2 or 3 wherein there is a collimator located between the polychromatic light source and said receptor so that light from the polychromatic light source passes through said collimator before passing into said receptor.

16. A device as claimed in any one of claims 1, 2 or 3 wherein the means for collecting said light after said light is directed onto said receptor is a lens, said lens being oriented and shaped to focus said light on a slit, said light passing through said slit to a second lens to collimate the light onto a diffraction grating, the means for taking absorbance measurements from at least one of the transmitted and reflected light from said light being a linear array detector, said detector having an output coupled to a microprocessor which is the means for taking the absorbance the measurements and is controlled by computer software to transform said measurements and determine the concentration level of at least one component of said mixture and produce a result.

17. A device as claimed in any one of claims 1, 2 or 3 wherein the near infrared region in which measurements are taken extends from 650 nm to 2800 nm.

18. A device as claimed in any one of claims 1, 2 or 3 wherein the near infrared region in which measurements are taken extends from 700 nm to 1100 nm.

19. A device as claimed in any one of claims 1, 2 or 3 wherein the means for taking absorbance measurements from at least one transmitted and reflected light from said collected light at several different wavelengths simultaneously is a linear array detector and a microprocessor, and there are means for reducing noise levels within said device by a scanning technique whereby the linear array detector scans the entire spectrum of interest many times per second for several repetitions ranging from approximately 8 to approximately 64 repetitions and the microprocessor then averages the results.

20. A device as claimed in any one of claims 1, 2 or 3 wherein the means for collecting said light after said light is directed onto said receptor are fibre optics that transmit said light to means for dispersing.

21. A device as claimed in any one of claims 1, 2 or 3 wherein the means for collecting said light after said light is directed onto said receptor is a hologram comprising means for focussing said light onto a diffraction grating.

22. A device as claimed in any one of claims 1, 2 or 3 wherein the means for dispersing said collected light into component wavelengths of said collected light is a holographic diffraction grating.

23. A device as claimed in claim 1 wherein the means for simultaneously taking measurement from at least one of transmitted and reflected light from said collected light over said continuum of wavelengths is a linear array detector coupled to microprocessor, said microprocessor having a memory constituting a means for comprising concentration level changes over a period of time.

24. A device as claimed in claim 22 wherein the linear array detector is a photo diode array and the means for dispersing said collected light into component wavelengths of said collected light is a grating, the light being collected from the grating by the photo diode array that is positioned to intercept the dispersed spectrum of light across its length.

25. A device as claimed in any one of claims 1, 2 or 3 wherein the concentration level of constituents that are measured are selected from, but not limited to, the group of: amino acid, nitrogen, blood oxygenation, carbon dioxide, cortisol, creatine, creatinine, glucose, ketones, lipids, fat, urea, amino acids, fatty acids, glycosolated hemoglobin, cholesterol, alcohol, lactate, $Ca++$, $K+$, $Cl-$, $HCO_3-$, and $HPO_4-$.

26. A device as claimed in any one of claims 1, 2 or 3 wherein the means for measuring concentration include one calibration equation for each constituent to be measured, each calibration equation including measurements taken at all of the wavelengths measured.

27. A device as claimed in any one of claims 1, 2 or 3 wherein there are means for transforming said measurements to enhance measurement of concentration of at least two constituents by using a calibration equation for each of said at least two constituents.

28. A non-invasive method for measuring concentration levels of blood and tissue constituents within a living subject such as a human or animal, using a polychromatic light source that emits a broad spectrum of light in the near infrared range from 650 nm to 2700 nm, said method comprising directing said light at a continuum wavelengths simultaneously onto a part of said subject, collecting the continuum of light after said light has been directed onto said part, focusing the collected light onto a grating, dispersing continuum of light into a dispersed spectrum of component wavelengths of said collected light onto a linear array detector, said linear array detector taking absorbance measurements of at least one of transmitted and reflected light from said collected light in said near infrared range simultaneously our said continuum of wavelengths said dispersed spectrum, scanning said linear array detector and passing said measurements to a microprocessor, taking a reference set of measurements, transforming said measurements over said broad range to enhance the measurement of concentration of at least one constituent from other constituents by using a calibration equation for said at least one constituent, determining the concentration level of at least one constituent of said blood and tissue and producing a result for each concentration level determined.

29. A method as claimed in claim 28 wherein the measurements are transformed to enhance the detection of at least one constituent from other constituents by taking a log of an inverse of at least one of the transmitted and reflected light from and further by calculating a second derivative of said log of said inverse.

30. A method as claimed in claim 29 including the step of producing the result on a display.

31. A method as claimed in any one of claims 27, 28 or 29 including the step of deriving the calibration equation from a least square's best fit of spectral data obtained using the device to actual measured levels obtained coincidentally.

32. A method as claimed in claim 28 wherein there are at least two constituents to be measured and the method includes the step of transforming said measurements to enhance the measurement of concentration of at least two constituents from other constituents by using a calibration equation for each of said at least two constituents.

33. A non-invasive method for measuring concentration levels of blood and tissue constituents within a living subject such as a human or animal, using a polychromatic light source that emits a broad spectrum of light in the near infrared range from 650 nm to 1100 nm, said method comprising simultaneously directing said continuum of light onto a part of said subject, collecting the continuum of light after said light has been directed onto said part, focusing the collected light onto a grating to disperse said collected continuum of light into a dispersed spectrum of component wavelengths of said collected light, dispersing said light onto a linear array detector, said linear array detector simultaneously taking absorbance measurements transmitted light from said collected light in said near infrared range over said continuum of, scanning said linear array detector and passing said measurements to a microprocessor, taking a reference set of measurements, transforming said measurements over said continuum of wavelengths to enhance the measurement of concentration of at least one constituent from other constituents by using a calibration equation for said at least one constituent and by taking a log of an inverse of said measurements and calculating a second derivative of said log, determining the concentration level of at least one constituent of said blood and tissue and producing a result for each concentration level determined.

* * * * *